US008849682B2

(12) United States Patent
Mahajan et al.

(10) Patent No.: US 8,849,682 B2
(45) Date of Patent: Sep. 30, 2014

(54) ADAPTIVE DATA STORAGE AND DOWNLOAD IN A MEDICAL DEVICE

(75) Inventors: Deepa Mahajan, Circle Pines, MN (US); Yanting Dong, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 836 days.

(21) Appl. No.: 12/887,852

(22) Filed: Sep. 22, 2010

(65) Prior Publication Data

US 2011/0082377 A1    Apr. 7, 2011

Related U.S. Application Data

(60) Provisional application No. 61/248,696, filed on Oct. 5, 2009.

(51) Int. Cl.
| | |
|---|---|
| *A61B 5/00* | (2006.01) |
| *H03M 7/30* | (2006.01) |
| *A61B 5/0452* | (2006.01) |
| *A61B 5/0205* | (2006.01) |
| *A61N 1/37* | (2006.01) |
| *A61B 5/04* | (2006.01) |
| *A61B 5/0432* | (2006.01) |
| *A61N 1/39* | (2006.01) |
| *A61N 1/372* | (2006.01) |
| *A61N 1/362* | (2006.01) |

(52) U.S. Cl.
CPC ............ *A61N 1/3702* (2013.01); *A61B 5/0205* (2013.01); *A61B 5/04012* (2013.01); *A61B 5/04325* (2013.01); *A61N 1/3962* (2013.01); *A61B 5/7232* (2013.01); *A61N 1/37252* (2013.01); *A61N 1/3621* (2013.01); *A61B 5/0002* (2013.01)
USPC .................................................. 705/3; 705/2

(58) Field of Classification Search
CPC ... A61B 5/7232; A61B 5/7264; A61N 1/3702
USPC ......................................................... 705/2–3
See application file for complete search history.

(56) References Cited

U.S. PATENT DOCUMENTS 5,506,872 A * 4/1996 Mohler ......................... 375/240
5,836,982 A * 11/1998 Muhlenberg et al. ............. 607/9
(Continued)

OTHER PUBLICATIONS

Kamboh, A M, et al., "Area-Power Efficient VLSI Implementation of Multichannel DWT for Data Compression in Implantable Neuroprosthetics", Michigan State Univ., East Lansing; Biomedical Circuits and Systems, IEEE Transactions on; vol. 1, Issue 2 http://ieeexplore.ieee.org//xpls/abs_all.jsp?arnumber=4374112, (Jun. 2007), 128-135.

(Continued)

*Primary Examiner* — Joy Chng
(74) *Attorney, Agent, or Firm* — Schwegman Lundberg & Woessner, P.A.

(57) ABSTRACT

In an example, a medical device includes a physiological data monitor (PDM), a memory, and a processor. The PDM is configured to monitor a physiological data parameter. The memory circuit is configured to store data collected by the PDM. The processor is configured to detect a data capture event and capture a first segment of physiological data associated with the data capture event. The processor is also configured to determine an amount of memory storage space available and determine a first priority level for the first segment of physiological data. The processor is further configured to determine a second priority level for a second segment of physiological data stored previously and select a processing scheme using the first and second priority levels. Finally, the processor is configured to process, using the processing scheme, the first and second segments of physiological data and store the first segment of physiological data.

21 Claims, 11 Drawing Sheets

(56) References Cited

U.S. PATENT DOCUMENTS

| | | | |
|---|---|---|---|
| 5,908,392 | A | 6/1999 | Wilson et al. |
| 6,285,909 | B1 | 9/2001 | Sweeney et al. |
| 6,526,314 | B1 | 2/2003 | Eberle et al. |
| 6,823,210 | B2 | 11/2004 | Eberle et al. |
| 6,917,830 | B2 | 7/2005 | Palreddy et al. |
| 6,978,182 | B2 | 12/2005 | Mazar et al. |
| 7,127,300 | B2 | 10/2006 | Mazar et al. |
| 7,395,117 | B2 | 7/2008 | Mazar et al. |
| 7,421,292 | B1 | 9/2008 | Kroll |
| 7,447,544 | B1 | 11/2008 | Kroll |
| 2004/0215270 | A1* | 10/2004 | Ritscher et al. ............. 607/27 |
| 2006/0094970 | A1 | 5/2006 | Drew |
| 2006/0094971 | A1 | 5/2006 | Drew |
| 2006/0094972 | A1 | 5/2006 | Drew |
| 2006/0095092 | A1 | 5/2006 | Drew |
| 2006/0155437 | A1* | 7/2006 | Wang et al. ............... 701/29 |
| 2006/0224202 | A1* | 10/2006 | Moffitt et al. ............. 607/17 |
| 2006/0235489 | A1 | 10/2006 | Drew et al. |
| 2006/0287691 | A1 | 12/2006 | Drew |
| 2007/0255147 | A1* | 11/2007 | Drew et al. ............... 600/509 |
| 2008/0064966 | A1 | 3/2008 | Brockway et al. |
| 2008/0132974 | A1 | 6/2008 | Strother et al. |
| 2008/0171922 | A1 | 7/2008 | Teller et al. |
| 2008/0188762 | A1 | 8/2008 | John et al. |
| 2008/0211665 | A1 | 9/2008 | Mazar et al. |
| 2008/0221633 | A1 | 9/2008 | Linker |
| 2008/0235469 | A1 | 9/2008 | Drew |
| 2008/0275309 | A1 | 11/2008 | Stivoric et al. |
| 2009/0058636 | A1 | 3/2009 | Gaskill et al. |
| 2009/0063193 | A1 | 3/2009 | Barton et al. |
| 2009/0076348 | A1 | 3/2009 | Manicka et al. |
| 2010/0280841 | A1 | 11/2010 | Dong et al. |

OTHER PUBLICATIONS

Kumar, Sunil, et al., "Ubiquitous Computing for Remote Cardiac Patient Monitoring: A Survey", Hindawi Publishing Corporation International Journal of Telemedicine and Applications, vol. 2008, Article ID 459185 ttp://portal.acm.org/citation.cfm?id=1453679, 19 pgs.

Strydis, Christos, et al., "Profiling of lossless-compression algorithms for a novel biomedical-implant architecture", http://ce.et.tudelft.nl/publicationfiles/1537_555_p109-strydis.pdf, Delft University of Technology, Delft, Netherlands International Conference on Hardware Software Codesign; Proceedings of 6th IEEE/ACM/IFIP international conference on Hardware/Software codesign and system synthesis. Atlanta, GA,Session: Exploration, prof, (2008), 109-114.

* cited by examiner

ADAPTIVE DATA STORAGE AND DOWNLOAD IN A MEDICAL DEVICE

CLAIM OF PRIORITY

This application claims the benefit of priority under 35 U.S.C. §119(e) of Mahajan et al., U.S. Provisional Patent Application Ser. No. 61/248,696, entitled "ADAPTIVE DATA STORAGE AND DOWNLOAD IN AN IMPLANTABLE DEVICE," filed on Oct. 5, 2009, which is herein incorporated by reference in its entirety.

BACKGROUND

Cardiac rhythm management (CRM) devices can include implantable devices that provide electrical stimulation to selected chambers of the heart in order to treat disorders of cardiac rhythm. For example, an implantable pacemaker can deliver timed pacing pulses to the heart to treat bradyarrhythmia, in which the heart rate can be too slow. In another example of a cardiac rhythm management device, an implantable cardioversion/defibrillator can deliver antitachyarrhythmia pacing (ATP) or a cardioversion or defibrillation shock to treat tachyarrhythmia, in which the heart rate can be too fast, and can also include pacing capability for bradyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF). Tachyarrhythmia can also occur in the atria. Examples include atrial fibrillation (AF) and atrial flutter (AFl). In yet another example, implantable cardiac resynchronization therapy (CRT) devices can deliver pacing-level pulses to spatially coordinate the heart contraction (with or without altering heart rate) for obtaining a more efficient contraction to improve cardiac output, and such capability can be combined with pacers, cardioverters, or defibrillators. In an even further example, implantable neurostimulation devices can be used to deliver electrical energy to a desired portion of the autonomic nervous system, such as to stimulate or inhibit one of the sympathetic or parasympathetic nervous systems to adjust an autonomic balance to impact cardiovascular performance.

CRMs are able to communicate with external devices using wireless communication methods such as radio frequency (RF) or mutual inductance. Some CRMs are able to obtain sampled values of the monitored heart activity signals or values of electrical signals provided by a sensor. The sampled heart activity signals are sometimes referred to as an electrogram. An electrogram can be stored in the CRM and later communicated to an external device where the sampled signals can be displayed for analysis. An electrogram can also be communicated to the external device from the CRM as the heart activity signal is sampled to provide real time electrograms. Along with electrogram data many other physiological parameters can be monitored and stored by CRMs (or other types of implantable medical devices). Retaining collected physiological data and presenting it in a meaningful manner to a treating physician can present challenges due to the limited storage and power capabilities present in CRM devices.

OVERVIEW

Cardiac rhythm management devices can be programmed with a number of different parameter settings that affect the manner in which therapy is delivered. These parameters can be initially programmed after implantation while a physician is monitoring the patient. In such a case, the physician may program the device based on electrogram or other physiological information available in the acute clinical setting. The patient's condition can later change, however. Capturing accurate electrogram or other physiological information obtained over a longer period of time, such as chronically between regularly-scheduled outpatient office visits, can help the physician re-program the device, if needed, or to diagnose and assess the patient's condition.

The present inventors have recognized, among other things, that traditional approaches to recording tachyarrhythmia or other episode data, are often limited by the restricted data storage space available within implantable medical devices (IMDs), such as CRMs. The present systems and methods address an IMD's restricted data storage space by employing a combination of data compression techniques and automated data downloading to an external device, among other things.

Example 1 is a system for adaptively managing physiological data within an implantable medical device. The system includes an implantable medical device. The implantable medical device includes a physiological data monitor, a memory circuit, and a processor circuit. The physiological data monitor is configured to monitor a physiological data parameter. The processor circuit can be coupled to the physiological data monitor and the memory circuit. The processor can be configured to detect a pathological episode using the monitored physiological data parameter. The processor can also be configured to determine an episode type for the pathological episode and capture, from the physiological data monitor, a segment of physiological data associated with the pathological episode. The processor can be further configured to select, using the episode type, a compression technique, from a plurality of compression techniques, to process the captured segment of physiological data and process the captured physiological data using the selected compression technique to produce a processed segment of physiological data. The processor can also be configured to store the processed segment of physiological data in the memory circuit for later use.

In Example 2, the system of Example 1 optionally includes the processor configured to determine an amount of remaining storage space available within the memory circuit. The processor can also be configured to select a compression technique, from a plurality of compression techniques using the amount of remaining storage space available within the memory circuit.

In Example 3, the system of one or any combination of Examples 1-2 optionally includes the processor configured to determine a device response to the pathological episode. The processor can also be configured to select a compression technique from a plurality of compression techniques using the determined device response to the pathological episode.

In Example 4, the system of one or any combination of Examples 1-3 optionally includes the processor configured to select a first compression technique when the device response includes delivering a shock. The processor can also be configured to select a second compression technique when the device response includes delivering anti-tachycardia pacing. The processor can further be configured to select a third compression technique when the device response includes diverting a therapy. In Example 4, the first compression technique is less lossy than the second compression technique and the second compression technique is less lossy than the third compression technique.

In Example 5, the system of one or any combination of Examples 1-4 optionally includes the processor configured to select the compression technique from a plurality of compression techniques using a result of evaluating a specified relationship between device response and episode type.

In Example 6, the system of Example 5 optionally includes the processor configured to receive the specified relationship between device response and episode type from an external source.

In Example 7, the system of one or any combination of Examples 1-6 optionally includes the processor configured to characterize a detected heart rate using a comparison of atrial versus ventricular rates to produce an AV comparison and select the compression technique from the plurality of compression techniques using the AV comparison.

In Example 8, the system of Example 7 optionally includes the processor configured to determine a device response to the pathological episode and select a compression technique from a plurality of compression techniques using the determined device response to the pathological episode and the AV comparison.

In Example 9, the system of one or any combination of Examples 1-8 optionally includes an external data storage and communication device to receive physiological data stored in the memory circuit. Example 9 also includes the processor configured to initiate, based on detecting a low memory circuit space condition, a communication link to the external data storage and communication device and transmit a portion of the physiological data stored in the memory circuit.

In Example 10, the system of Example 9 optionally includes the processor configured to transmit a portion of the physiological data stored in the memory circuit by transmitting the oldest data to the external data storage and communication device first.

Example 11 is a method for adaptively managing physiological data within an implantable medical device. The method includes monitoring a physiological data parameter and detecting a pathological episode using the monitored physiological data parameter. The method also includes determining an episode type for the pathological episode and capturing a segment of physiological data associated with the pathological episode. The method further includes selecting, using the episode type, a compression technique, from a plurality of compression techniques, to process the captured segment of physiological data and processing the captured physiological data using the selected compression technique to produce a processed segment of physiological data. The method of Example 11 concludes by storing the processed segment of physiological data for later use.

In Example 12, the method of Example 11 optionally includes the selecting the compression technique further including determining an amount of remaining storage space available within the implantable medical device and using the amount of remaining storage space to select the compression technique.

In Example 13, the method of one or any combination of Examples 11-12 optionally includes determining a device response to the pathological episode, wherein the selecting the compression technique uses the device response to the pathological episode.

In Example 14, the method of Example 13 optionally includes the selecting the compression technique further including selecting a first compression technique when the device response includes delivering a shock, selecting a second compression technique when the device response includes anti-tachycardia pacing, and selecting a third compression technique when the device response includes diverting a therapy. In Example 14, the first compression technique provides less compression than the second compression technique and the second compression technique provides less compression than the third compression technique.

In Example 15, the method of one or any combination of Examples 13-14 optionally includes the selecting the compression technique including using a result of evaluating a specified relationship between device response and episode type.

In Example 16, the method of Example 15 optionally includes the selecting the compression technique including receiving the specified relationship between device response and episode type from an external source.

In Example 17, the method of one or any combination of Examples 11-16 optionally includes the selecting the compression technique including characterizing a detected heart rate using a comparison of atrial versus ventricular rate to produce an AV comparison and using the AV comparison to select the compression technique from the plurality of compression techniques.

In Example 18, the method of Example 17 optionally includes the selecting the compression technique including determining a device response to the pathological episode and using the device response to the pathological episode and the AV comparison.

In Example 19, the method of one or any combination of Examples 11-18 optionally includes the storing the processed segment of physiological data including initiating, based on detecting a low memory circuit space condition, a communication link to an external data storage and communication device and transmitting a portion of the physiological data stored in the memory circuit.

In Example 20, the method of Example 19 optionally includes the transmitting the portion of the physiological data stored in the memory circuit transmits the oldest data to the external data storage and communication device first.

Example 21 is an implantable medical device. The implantable medical device includes a physiological data monitor, a memory circuit, and a processor circuit. The physiological data monitor can be configured to monitor a physiological data parameter. The memory circuit can be configured to store data collected by the physiological data monitor. The processor circuit can be coupled to the physiological data monitor and the memory circuit. The processor can be configured to detect a physiological data capture event and capture, from the physiological data monitor, a first segment of physiological data associated with the physiological data capture event. The processor can also be configured to determine an amount of memory circuit storage space available and determine a first priority level for the first segment of physiological data. The processor can further be configured to determine a second priority level for a second segment of physiological data stored on the memory circuit and select a processing scheme for the first and second segments of physiological data using the first and second priority levels, the processing scheme including a compression technique. Finally, the processor can be configured to process, using the processing scheme, the first and second segments of physiological data and store the first segment of physiological data in the memory circuit for future use.

In Example 22, the implantable medical device of Example 21 optionally includes the processor further configured to select a first processing scheme when the first priority level is higher than the second priority level, the first processing scheme using a first compression technique on the first segment of physiological data and a second compression technique on the second segment of physiological data and select a second processing scheme when the second priority level is higher than the first priority level, the second processing scheme using a first compression technique on the second segment of physiological data and a second compression technique on the first segment of physiological data. In Example 22, the first compression technique is less lossy than the second compression technique and wherein a higher priority level indicates greater importance.

In Example 23, the implantable medical device of Example 22 optionally includes the processor further configured to transmit the portion of the physiological data stored in the memory circuit including the first segment of physiological data when the first priority level is higher than the second priority level and transmit the portion of the physiological data stored in the memory circuit including the second segment of physiological data when the second priority level is higher than the first priority level.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
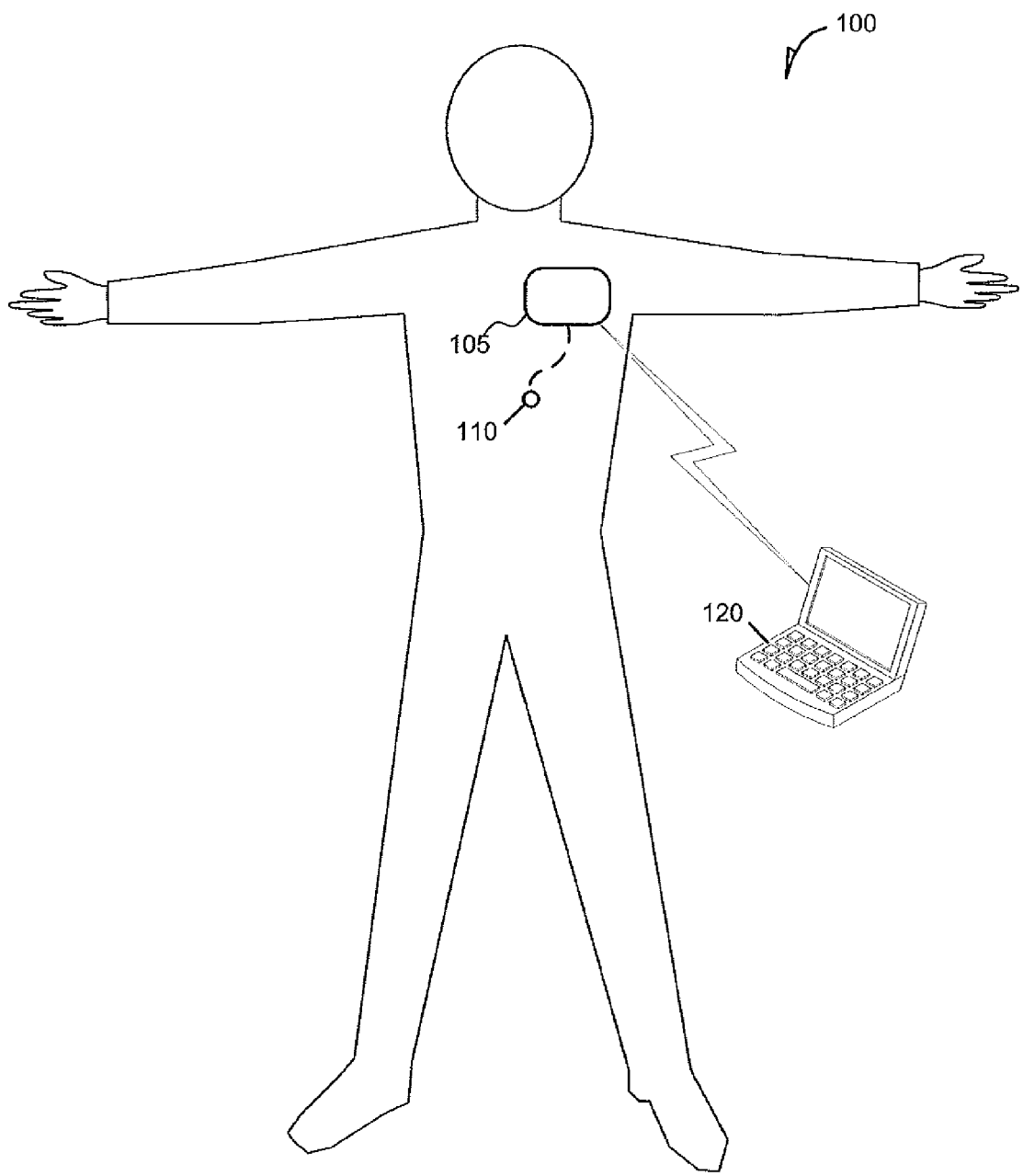
FIG. 1 is a block diagram illustrating an example of an implantable cardiac function management system communicatively coupled to an external communication device.

As described above, some IMDs can be used to provide pacing therapy to patients who have cardiac rhythm problems. For example, an implanted CRM device can be used to provide pacing therapy to a patient with sinus node dysfunction, where the heart fails to properly initiate depolarization waves, or an atrio-ventricular condition disturbance, wherein the conduction of depolarization waves through the heart tissue is impaired.

Many modern IMDs are capable of communicating with devices located outside of the body. These external devices can be used to receive information from the IMDs including sensor information and information about events, such as when the IMD has provided therapy (also referred to as the device response). In some cases, the external communication or interface device can also transmit operational parameters to the IMD, or in other words program the IMD.

These external communication and programming devices can be provided to a patient and are often located within the patient's home. These external devices can provide information to a computerized patient management system designed to assist in monitoring the patient's condition. An exemplary remote patient. management system is the LATITUDE® patient management system from Boston Scientific Corporation, Natick Mass. Exemplary aspects of a remote patient management and monitoring system are also described in ADVANCED PATIENT MANAGEMENT SYSTEM INCLUDING INTERROGATOR/TRANSCEIVER UNIT, U.S. Pat. No. 6,978,182 to Mazar et al., which is incorporated by reference herein.

Patient management systems, such as LATITUDE® can provide large amounts of data about patients with implanted medical devices back to a treating physician. For example, these systems can store information about patient characteristics, patient sensor readings including electrocardiogram (EGM), device settings, and delivery of therapy by the device. The sensor readings can include information associated with an arrhythmia episode or other pathological episodes experienced by the patient.

"Arrhythmia episode" can be regarded as a time period of particular interest when there is abnormal activity, for example, abnormal cardiac activity. "Episode data" can include sensor readings from a medical data-generating device before, during and after the episode, and can also include device settings, actions that were taken by the device and other information. This document describes, among other things, an episode database or IMD memory that stores episode data about episodes that have occurred. Episode data can include physiological data.

The episode data or part of the episode data for a particular episode can be analyzed using an adjudication algorithm to determine an arrhythmia classification and other types of characterization data about the arrhythmia episode. The characterization data can be stored in an adjudication database. In some examples, the characterization data is sent to the data-generating device to be stored. Once an arrhythmia classification has been generated for a particular episode or a group of episodes, then it is possible to provide patients and clinicians with many different types of reports related to the episode data. It is also possible for the system to analyze the characterization data to provide programming recommendations for the data-generating device where certain conditions are present. It is also possible to query the adjudication database for many different types of information that may be useful to clinicians, researchers or regulators.

Episode adjudication can be done directly on the IMD within an on board processor, sometimes referred to as an adjudication processor. An adjudication processor can be capable of extracting certain features from the episode data which are very helpful in properly classifying the arrhythmia episode. The features can be based on domain knowledge used by physicians to classify the episode data. For example, the electrogram can be used to determine if the arrhythmia episode originates from the atrium or ventricle of the heart through analyzing the timing of the atrial and ventricle activities. The determination can alternatively or additionally be based on the morphology information from the electrograms from different atrial and ventricular channels.

In an example, the adjudication processor is operatively connected to the IMD memory and is configured to receive as input episode data regarding one of the different arrhythmia episodes. The adjudication processor can use an automated method or algorithm to generate characterization data about the arrhythmia episode. More than one algorithm can be used. For example, different algorithms can be used for different applications. Examples of classification algorithms that can be used for the adjudication algorithm include decision tree algorithms, Naïve Bayes algorithms, support vector machine algorithms, or other pattern recognition algorithms.

One example of episode classification or type determination is an arrhythmia classification. The characterization data can be stored in an adjudication database, which can be stored in an IMD's memory. In an example, the options for the arrhythmia classification include monomorphic ventricular tachycardia (MVT), polymorphic ventricular tachycardia/ventricular fibrillation (PVT/VF), supraventricular tachycardia (SVT), atrial-ventricular (AV) nodal reentrant tachycardia (AVNRT), atrial fibrillation (AF), atrial flutter (AFL), atrial tachy (AT), sinus tachy (ST), dual tachy (DT), pacemaker-mediated tachycardia (PMT), one-to-one AV ratio with constant ventricular morphology, oversensing, noise, or indeterminate. It is also possible for the system to provide more or fewer arrhythmia classifications than those listed. In an example, the arrhythmia classification options include at least MVT. In an example, the arrhythmia classification options include at least polymorphic ventricular tachycardia/ventricular fibrillation (PVTNF), monomorphic ventricular tachycardia (MVT) and atrial fibrillation (AF). In various examples, there are three or more, four or more, five or more and six or more options for the arrhythmia classification.

Additional information concerning adjudication of episodes to classify the particular type of episode is detailed in ADJUDICATION OF ARRHYTHMIA EPISODE DATA SYSTEMS AND METHODS, U.S. Patent Application No. 61/175,232, to Cardiac Pacemakers, Inc, of St. Paul, Minn., which is incorporated by reference herein.

As highlighted above, the proper programming and maintenance of an IMD can involve frequent or constant monitoring of a patient's changing conditions. In order to achieve optimal programming of a CRM device, a physician needs greater insights into the operation of the CRM device within a specific patient over a period of time, such as a chronic period of time between outpatient office visits. Information regarding episodes where the IMD is delivering therapy (or should have delivered therapy) is particularly important to capture. These pathological episodes can include arrhythmia, ventricular tachycardia (VT), polymorphic ventricular tachycardia (VF/PVT), supraventricular tachycardia (SVT), Monomorphic VT (MVT), and atrial fibrillation (AF), among others. To this end, an IMD can include onboard memory to record physiological data monitored by the IMD.

As described above, when attempting to re-program a CRM device, physicians can benefit from detailed information regarding device performance, especially information about pathological episodes, such as an arrhythmia or the like. The following describes methods and systems for providing physicians with detailed information, such as electrogram (EGM) data, through the use of multiple data compression techniques coupled with automated download to external communication devices.

Implantable Device and Related Systems

FIG. 1 is a block diagram illustrating an example of an implantable cardiac function management system communicatively coupled to an external communication device. In this example, the system 100 can include an implantable medical device (IMD) 105, a physiological data sensor 110, and an external communication device 120. In an example, the IMD 105 is a cardiac rhythm management (CRM) device used to provide cardiac rhythm therapy to a patient's heart. In an example, the physiological data sensor 110 can be used to detect EGM data, such as including both sensed and evoked response depolarization information. In another example, the physiological data sensor 110 can be used to monitor one or more other physiological parameters related to cardiac operations, such as heart rate, respiration rate, or blood pressure, among others. In some examples, multiple physiological data monitors can be employed to monitor multiple relevant physiological parameters.

Figure 2:
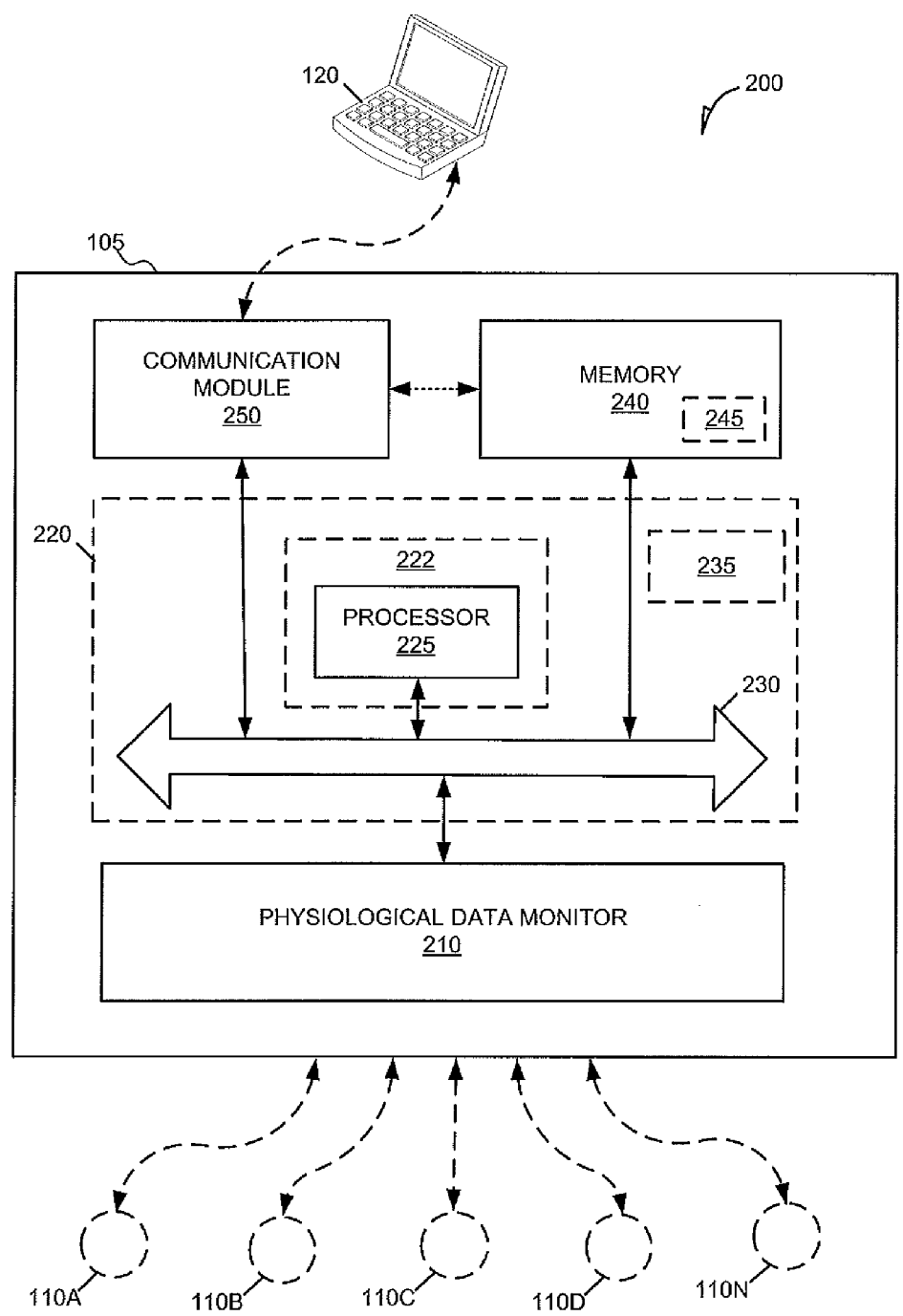
FIG. 2 is a block diagram illustrating an example of an implantable cardiac function management system configured to enable adaptive data storage and download.

The external communication device 120 can be used for programming the IMD 105, displaying data obtained from the IMD 105, or for communicating data downloaded from the IMD 105 to a physician or central monitoring station (not shown). In an example, the external device can include a personal computer, such as a laptop, configured to communicate with the IMD 105. In an example, the external device communicates via a hardwired communication link with the IMD 105. In an example, the external communication device 120 communicates over a wireless communication link with the IMD 105. In an example, the external communication device 120 can receive data from the IMD 105 and display that, such as on a computer display. In an example, the external communication device 120 can also receive wireless communications initiated by the IMD 105 for the purpose of downloading stored episode data for use by a physician in diagnosis or device programming. In this example, the external communication device 120 can forward the data downloaded by the IMD 105 to a central monitoring station over wired or wireless data connections. The wired data connections can include a digital subscriber line, cable modem, or a dial-up connection over a plain old telephone (POTS) line. This type of communication of data collected by an IMD 105 is further explained in IMPLANTABLE MEDICAL DEVICE HAVING LONG-TERM WIRELESS CAPABILITIES, U.S. Pat. No. 7,395,117 to Mazar et al., which is incorporated by reference herein. This type of communication and IMD 105 interaction with an external communication device is also further explained in METHOD AND APPARATUS FOR ENABLING DATA COMMUNICATION BETWEEN AN IMPLANTABLE MEDICAL DEVICE AND A PATIENT MANAGEMENT SYSTEM, U.S. Pat. No. 7,127,300 to Mazar et al., which is also incorporated by reference herein, FIG. 2 is a block diagram illustrating an example of an implantable cardiac function management system configured to enable adaptive data storage and download. In an example, a system 200 can include an implantable medical device 105, one or more physiological data sensors 110A, 110B, . . . , 110N (collectively hereinafter referred to as 110), and an external communication device 120. In an example of the system 200, the IMD 105 can include a physiological data monitor 210, a processing module 220, a memory 240, and a communication module 250. In some examples, the processing module 220 can include a processor 225 and a communication bus 230. In certain examples, the processing module 220 can also include a pathology detection circuit 222. The pathology detection circuit includes the processor 225 and is communicatively coupled to the physiological data monitor 210. For example, signal sampling circuitry within the physiological data monitor 210 can present digitized values of an electrical signal produced by the sensors 110 to the pathology detection circuit 222.

In some examples, the pathology detection circuit 222 includes the processor 225 and performs one or more detection algorithms that are embodied in instructions in software or firmware that are performable by the processor 225. Such a processor may include a microprocessor, a digital signal processor (DSP), or application specific integrated circuit (ASIC).

In some examples, the processing module 220 can also optionally include processor specific memory 235 used to store data being manipulated by the processor 225 or the pathology detection circuit 222. In an example, the communication bus 230 can enable communication between the physiological data monitor 210, the processor 225, the memory 240, and the communication module 250. The memory 240 and the communication module 250 can optionally communicate directly without routing through the communication bus 230. In certain examples, the memory 240 can include a main memory as well as one or more secondary memory circuits 245. In an example, the secondary memory circuits 245 can be used to temporarily store data while a connection to the external communication device 120 is established.

In an example, the physiological data monitor 210 can receive data from one or more physiological data sensors 110. In certain examples, the physiological data sensors 110 can include sensors implanted within the patient's body, also referred to as internal sensors. In other examples, the physiological data sensor(s) 110 can include ambulatory or other external sensors such as worn or carried by the patient or adhered to a patient's skin or worn against a patient's skin. In some examples, the physiological data sensors 110 can include both external and internal sensors. In an example, the physiological data sensors 110 can include one or more of a heart sound sensor, a blood pressure sensor, a posture sensor, a respiratory sensor, an activity sensor, or a chemical sensor. In this example, the physiological data monitor 210 can be configured to receive data from any or all of the sensors and to communicate the received data, such as to other portions of the IMD 105 or to an external communication device 120 via the communication module 250, In certain examples, the sensors 110 can provide a time-varying electrical signal that is related to physiologic cardiovascular events of a subject. A non-exhaustive list of examples of such sensors 110 include a cardiac signal sensing circuit, an intracardiac impedance sensing circuit, a transthoracic impedance sensing circuit, a blood pressure sensor, a blood gas sensor, a chemical sensor, a heart sound sensor, a posture sensor, and an activity sensor. In some examples, the IMD 105 communicates with a sensor external to the IMD (not shown). The signals provided by this variety of sensors can be used to detect a pathological event or episode that a patient or subject is experiencing or has experienced.

For example, the IMD 105 may be able to detect an arrhythmic event from a cardiac signal sensed using any of the electrodes described. The cardiac signal is representative of cardiac activity of a subject or patient. When a pathological episode such as an episode of arrhythmia is detected, the IMD 105 may begin recording the cardiac signal (e.g., as an electrogram). The recorded cardiac signal, referred to generally as physiological data or monitored physiological data, may then be communicated to an external device. However, in general, every pathological episode detected by an IMD 105 is stored in internal memory, such as memory 240.

Returning to FIG. 2, once received, the monitored physiological data can be transferred to the processor 225 or stored directly in memory 240. In this example, the memory 240 can be accessed by the external communication device 120 through the communication module 250. In some examples, the communication module 250 communicates to the external communication device 120 over a communications link. As discussed above, the communications link between the external communication device 120 and the IMD 105 can be either wired or wireless.

Methods

Figure 3:
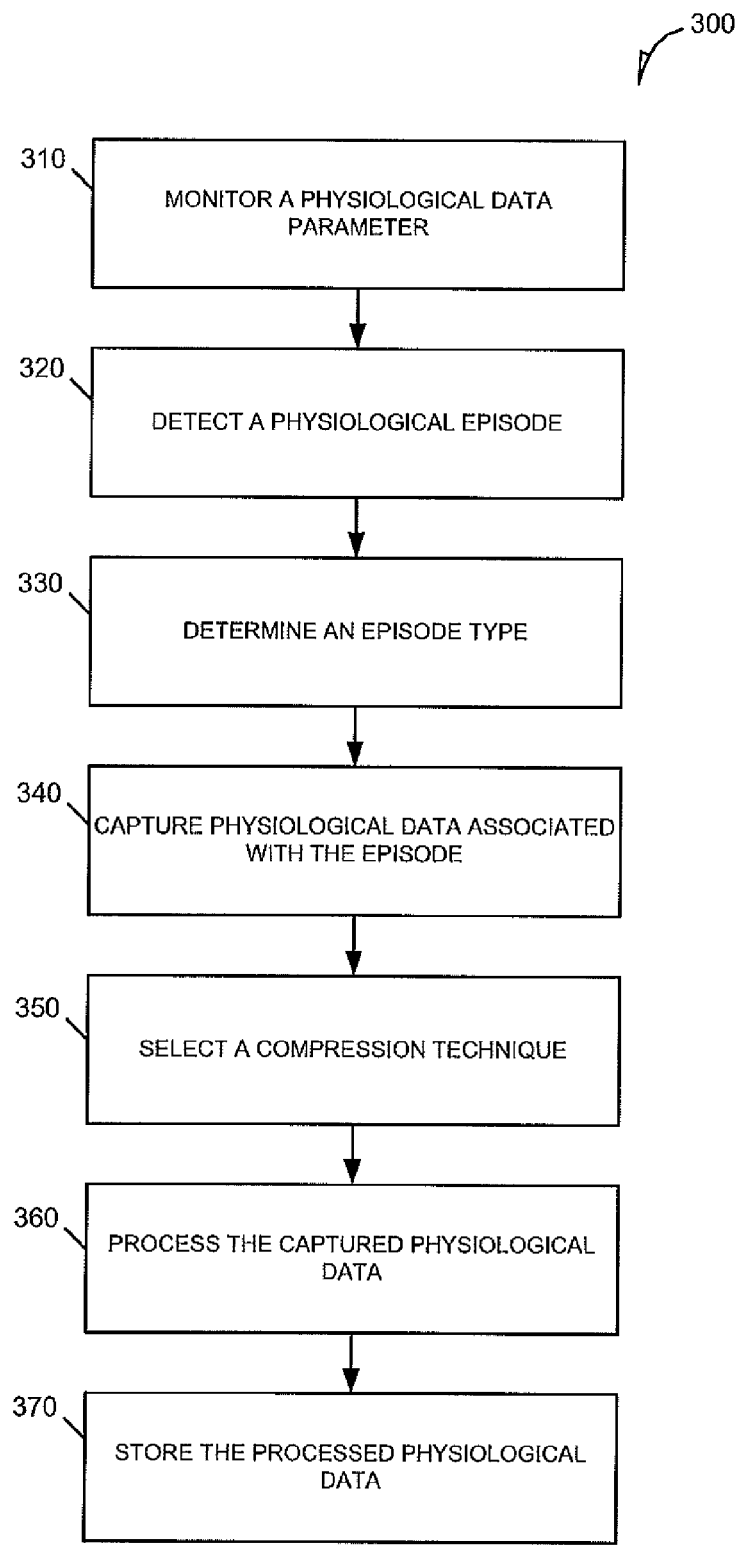
FIG. 3 is a flowchart illustrating an example of a method of adaptive data storage using multiple compression techniques in an implantable device.

FIG. 3 is a flowchart illustrating an example of a method of adaptive data storage using multiple compression techniques in an implantable device. In an example, a method 300 includes monitoring a physiological data parameter 310, detecting a pathological episode 320, determining a possible episode type 330, capturing physiological data associated with the episode 340, selecting a compression technique 350, processing the captured physiological data 360, and storing the processed physiological data. The method 300 begins at 310 with the physiological data monitor 110 monitoring a physiological data parameter, such as heart rate or respiration rate. In an example, the physiological data monitor can use one or more of the physiological data sensors 110 to obtain the monitored parameter from the patient.

At 320, the method 300 continues with the processor 225 detecting a pathological episode, such as a tachyarrhythmia. The detection of an episode can be triggered by one or many different events, an example can include a rapid heart rate (e.g., within a tachyarrhythmia rate zone, e.g., exceeding 150 bpm) or a sudden increase in respiration without a corresponding detection of physical exertion. In some examples, the pathological episode is an episode of tachyarrhythmia such as, among other things, VT, VF, SVT, sinus tachycardia (ST), AF, or AFl. In certain examples, the IMD 105 senses cardiac depolarization signals and detects tachyarrhythmia by detecting a depolarization rate that exceeds a tachyarrhythmia detection rate threshold and that the depolarization rate is sustained for a period of time.

Although this example has focused on heart rate, detection of a pathological episode can be triggered by any number of physiological data parameters or statistics kept by the IMD 105. Some examples of physiological data parameters can include heart rate, respiration rate, electrogram morphology, blood pressure, blood gas, blood chemistry, atrial versus ventricular heart rate, or heart rate stability. In certain examples, the detection of an episode can include a combination of multiple physiological data parameters. In some examples, an episode can be detected when the rate of change of a monitored physiological data parameter meets a specified test. In an example, meeting the specified test can include exceeding a threshold rate of change, for example, a rapid acceleration in heart rate. In these examples, the IMD 105 can also be configured to qualify or disregard a rapid rate of change if physical exertion is also detected. In an example, meeting the specified test can include transgressing a specified threshold for template match. For example, electrogram morphology differs from presenting electrogram template by more than a specified threshold. In another example, an episode can be detected when lead impedance is found to be out of bounds. In an example, episode detection parameters can be programmed by a physician, allowing the physician the ability to target certain parameters, conditions, or device operations.

In certain examples, operation 320 can also include a device response to the detected physiological episode. For example, if the device determines that the detected physiological episode is an atrial fibrillation the IMD 105 can deliver a programmed therapy, such as a shock. The type of therapy delivered by the IMD 105 can factor into the level of compression applied to the storage of the physiological data collected.

At 330, the method 300 continues with the processor 225 determining an episode type, such as ventricular tachycardia (VT) or monomorphic ventricular tachycardia (MVT). The processor 225 can use data provided by the physiological data monitor 210 to determine the episode type. Classifying episode types is discussed at length above. In addition, noise can be classified by looking at number of turns about an axis in a signal. Additional information on noise classification is detailed in METHOD AND SYSTEM FOR NOISE MEASUREMENT IN AN IMPLANTABLE CARDIAC DEVICE, U.S. Pat. No. 6,917,830 to Palreddy et al., which is incorporated by reference herein.

The method 300 continues at 340 by capturing physiological data associated with the episode. In an example, a segment of physiological data is collected from the physiological data monitor 210 and stored temporarily in either the memory 240 or in the processor memory 235. At 350, the method 300 uses the processor 225 to select a compression technique. The selection of a compression technique can include evaluation of the episode type, the available space in the memory 240, or the type of IMD response to the episode, among other things. At 350, the method 300 can select from multiple available compression techniques depending upon how important the data may be to a physician in future diagnosis or device programming. The compression techniques implemented in an example IMD can range from lossless low compression techniques to lossy high compression techniques. Various algorithms can be used to compress data at variable compression ratios (e.g., 2:1, 4:1, 8:1, 16:1). Note that, in general the higher compression ratios result in higher data loss during compression. Compression ratios can be selected on the basis of data priority, with lower priority data compressed with higher compression ratios. Additional information on envisioned compression techniques is discussed below in a separate section named Compression Techniques.

At 360, the method 300 continues with the processor 225 processing the captured physiological data with the selected compression technique. Compressing the captured physiological data allows more data to be retained within the IMD's limited memory 240. However, as mentioned above, some compression techniques can cause a loss of data (e.g., the original captured data may not be one hundred percent recoverable). The potential loss of detail within certain data types is one of the reasons for implementation of multiple compression techniques. As mentioned above, potential loss of data is also the reason for allowing for programmable selection of compression level based on factors such as episode type, device response, and heart rate characterization. Additional factors for compression technique selections are discussed below in reference to FIG. 4.

The method 300 concludes at 370 by storing the processed physiological data in the memory 240. In certain examples, the processor 225 sends the processed data over the communication bus 230 to the memory 240. The processed physiological data can be retained within the memory 240 until downloaded to the external communication device 120 via the communication module 250. Alternatively, the processed physiological data can be retrieved through wired or wireless connections when the patient visits a treating physician's office.

Figure 4:
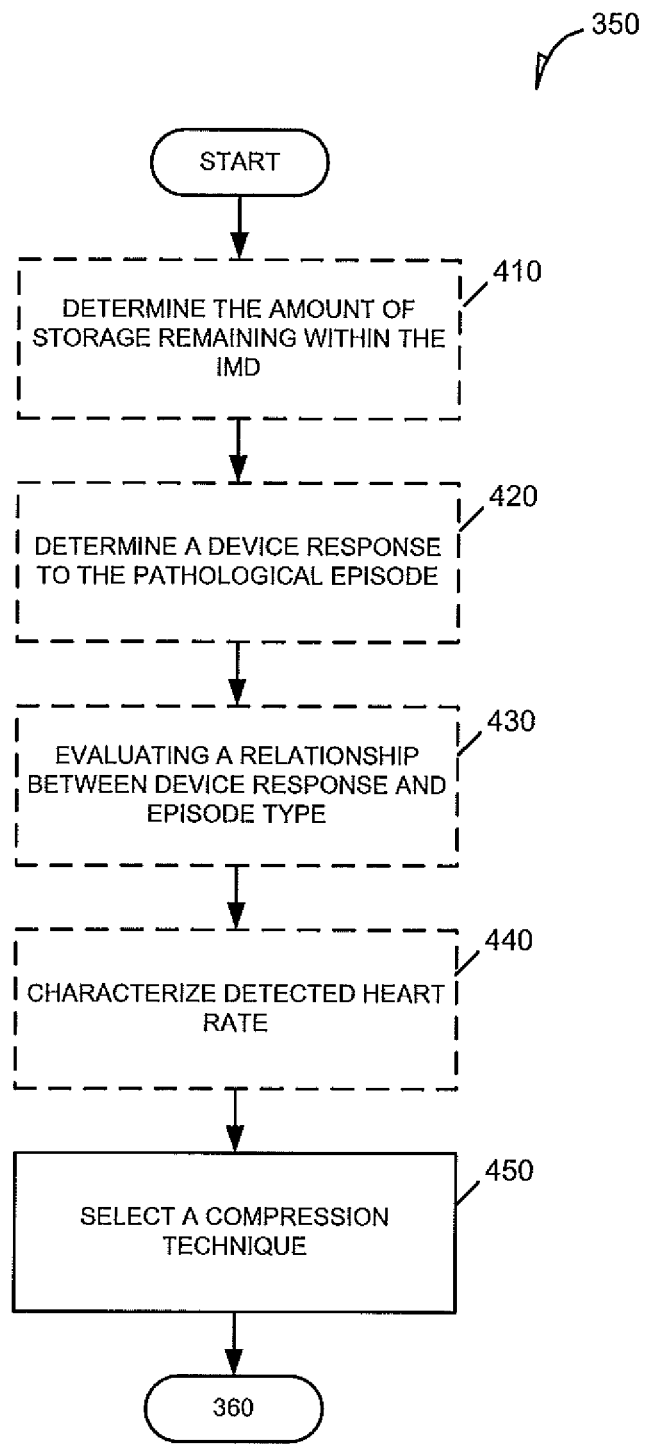
FIG. 4 is a flow chart illustrating various optional methods of selecting a compression technique for compressing physiological data collected by an implantable device.

FIG. 4 is a flow chart illustrating various optional methods of selecting a compression technique for compressing physiological data collected by an implantable device. In an example, the method 350 includes determining the amount of storage remaining within the TMD 410, determining a device response to the pathological episode 420, evaluating a relationship between device response and episode type 430, characterizing detected heart rate to produce an AV comparison 440, and selecting a compression technique 450 using one or more of 410-440. Table 1 illustrates an example matrix of selection criteria for selecting a compression technique for compressing physiological data collected by an IMD 105.

TABLE 1

Compression Technique Selection Matrix

| Heart Rate Characterization | Device Response | Episode Type | Compression Type |
|---|---|---|---|
| A = V | Shock | SVT | Compression Technique One* or no compression |
| V > A | Shock | MVT | Compression Technique Two* on RV Channel, and Compression Technique Four* on A channel |
| A > V | Therapy Diverted | AF/SVT | Compression Technique Three* Or Compression Technique two on A channel and compression technique four on V channel |
| N/A | N/A | Noise | No compression (or store shorten snippets of data if memory is low) |
| V > A | Shock | VF/PVT | Compression Technique four* |
| A > V | Shock | AF | No Compression |

*Where compression technique three is more lossy than compression technique two and compression technique two is more lossy than compression technique one, etc . . .

Compression techniques can also be determined by the condition detected and treated by the implanted devices. For example, in the implantable device, a morphology based algorithm can be used to detect ventricular tachycardia and supra-ventricular tachycardia. An example implementation of a morphology based algorithm is the RHYTHM ID feature in the Boston Scientific ICD/CRT-D devices. Rhythm ID stores the normal sinus beat morphology on a regular basis. When a tachyarrhythmia is detected, if the morphology matches the previous stored normal sinus rhythm, it is deemed as a supra-ventricular tachycardia and the therapy can be withheld, otherwise, it is treated as a ventricular tachycardia. The match and no-match decision is based on the correlation coefficients between the tachycardia rhythm and normal sinus-rhythm: if the correlation coefficient is higher than a threshold, it is a match, otherwise, it is not a match. In some tachyarrhythmias, the correlation coefficient may be very close to the threshold. For those episodes, no matter what the therapy decision was made by the implantable device, no-compression or compression with compression techniques with no loss should be used. For the episodes with correlation coefficients much larger or smaller than the predetermined threshold, a more lossy compression technique may be used.

The method 350 can include any combination of operations 410 through 440 to select an appropriate compression technique to use on the newly captured physiological data, or in some examples, to use on physiological data already stored within the memory 240 to make additional space for the newly captured data.

The method 350 can begin at 410 by determining the amount of storage remaining within the IMD 105. In some examples, the processing module 220 maintains a running total of remaining storage space within the memory 240. In other examples, the processing module 220 can query the memory 240 to determine available space. The amount of available storage space can be managed to ensure that any high priority (e.g., important to clinical diagnosis or device programming) episode data is able to be recorded by the IMD 105.

At 420, the method 350 determines the device response to the pathological episode, which can include both therapy delivered to the episode as well as the decision process by the IMD 105 on how the therapy decision was made. In some examples, operation 420 can also include determining device diagnostics obtained by the IMD 105. As depicted in Table 1 different episode types can tolerate different levels of compression and still retain useful data for future diagnosis and device programming. For example, an AF where no device response was provided can be compressed with a lossy compression technique and still provide a physician with useful information about the episode. Conversely, if the episode is classified as noise, but the device responded by delivering a shock, the treating physician is going to want to sec as detailed information as can be recorded by the IMD 105. Thus, in this scenario no compression should be applied to the physiological data recorded about the episode. In another example, if noise is detected by the IMD 105, but no therapy is delivered, the noise data can be compressed or a short segment can be recorded without any additional compression. This process of evaluating the relationship between device response and episode type is done by the method 350 at 430.

At 440, the method 350 can use the processing module 220 to characterize the detected heart rate. In some examples, the heart rate is characterized to determine whether there is any rate differential between the sensed atrial heart rate and the sensed ventricular heart rate. In these examples, the heart rate characterization at 440 can produce an AV comparison that can be used to further refine compression technique selection. In certain examples, the AV comparison can be used to select compression techniques for atrial and ventricular channels individually. Other methods of using heart characterization can also be implemented.

The method 350 concludes at 450 with the processing module 220 selecting a compression technique using one or more of the methods and parameters described in relationship to operations 410 through 440. For example, the processing module 220 can use the device response to the pathological episode from operation 420 and the heart rate characterization from operation 440 to select from a plurality of compression techniques. In another example, the processing module 220 can use the results of evaluating the relationship between device response and episode type from operation 430 along with the amount of storage space remaining from operation 410 to select a compression technique. In certain examples, selecting a compression technique at 450 results in selecting no compression to be applied to the physiological data under the current set of circumstances.

Figure 5:
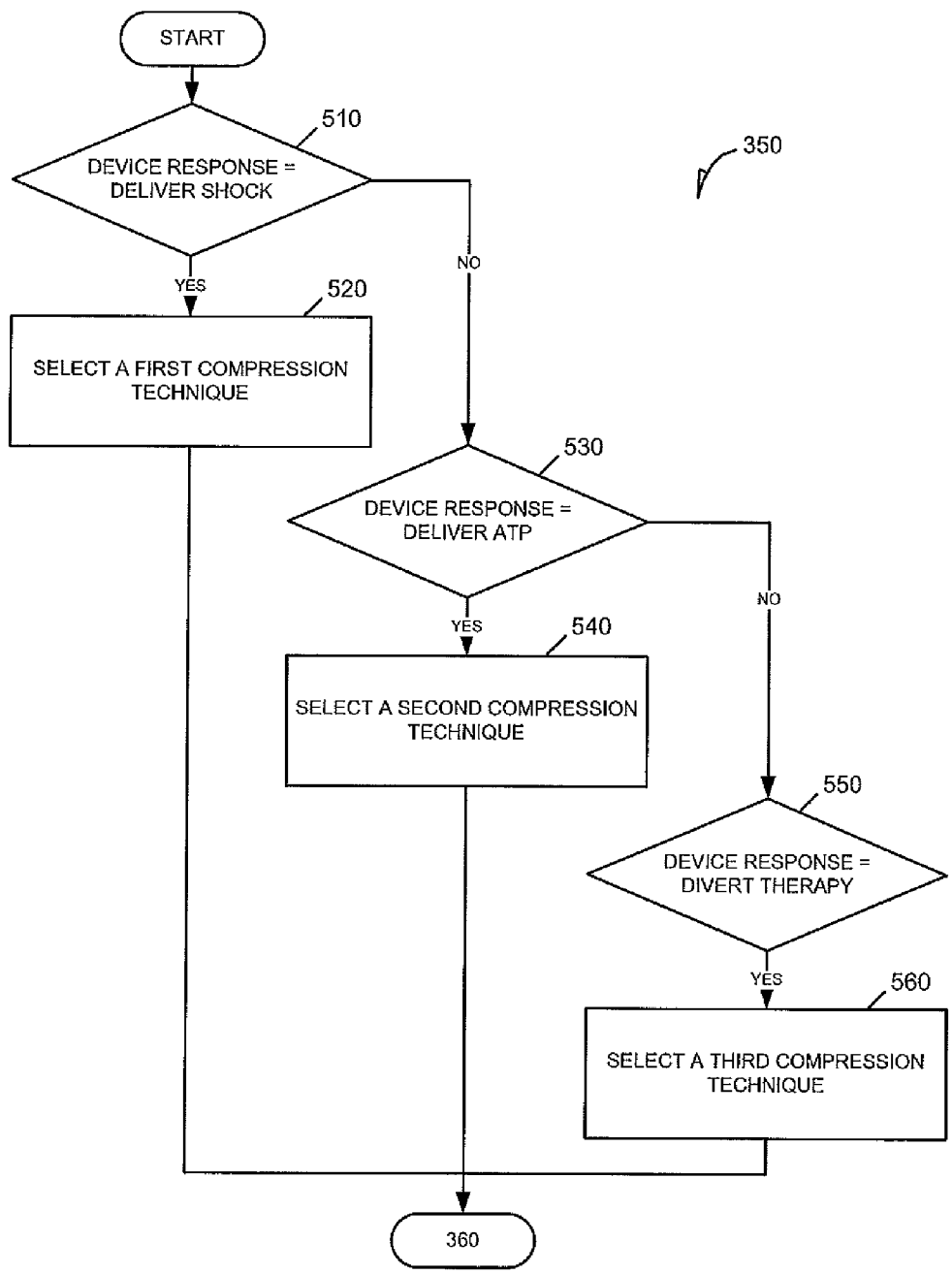
FIG. 5 is a flowchart illustrating an example method for selecting a compression technique to compress physiological data collected by an implantable medical device.

FIG. 5 is a flowchart illustrating an example method for selecting a compression technique to compress physiological data collected by an IMD 105. The method 350 illustrated in FIG. 5 includes determining device response 510, 530, 550 and selecting a compression technique 520, 540, 560. The method 350 illustrated in FIG. 5 depicts one specific example for compression technique selection. At 510 the processing module 220 determines if the device response to the current episode was to deliver a shock. If a shock was delivered a first compression technique is selected at operation 520. If a shock was not delivered, at 530 the processing module determines whether anti-tachycardia pacing (ATP) was delivered by the device. If ATP was the IMD's 105 response to the current episode, then at 540 the processing module 220 selects a second compression technique. At 550, the processing module determines that therapy for the current episode was diverted, and then a third compression technique is selected at 560.

Figure 6:
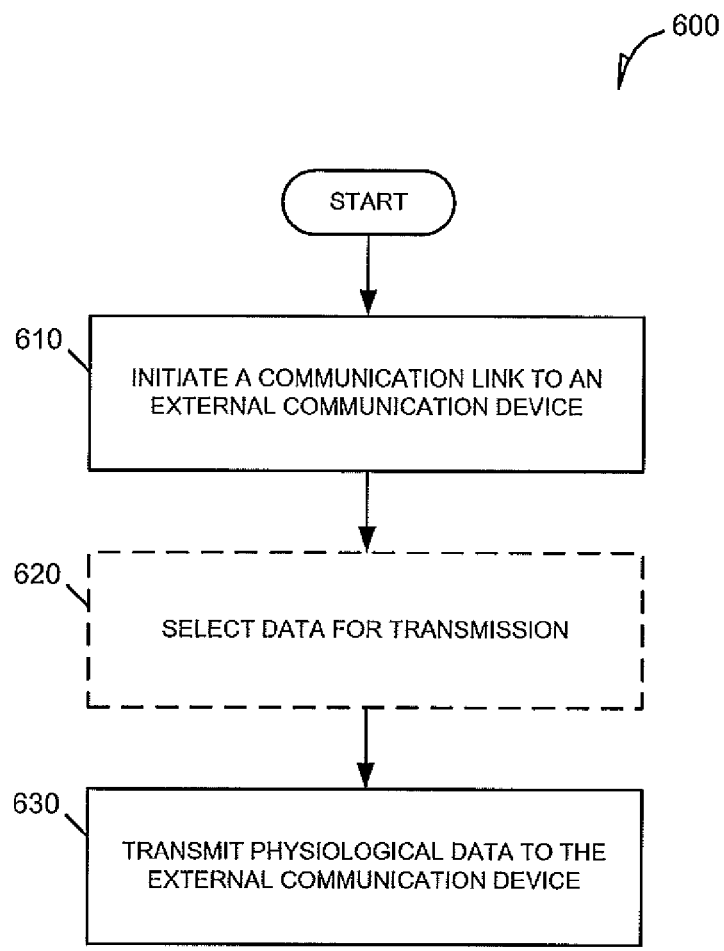
FIG. 6 is a flowchart illustrating an example method for downloading physiological data collected by an implantable medical device to an external device.

FIG. 6 is a flowchart illustrating an example method 600 for downloading physiological data collected by an IMD 105 to an external communication device 120. A method 600 includes initiating a communication link to an external communication device 610 and transmitting physiological data to the external communication device 630. In certain examples, the method 600 can also include selecting data for transmission 620. The method 600 begins at 610 with the communication module 250 initiating a communication link to the external communication device 120. In some examples, the communication link is established over a short range wireless communication protocol, such as BLUETOOTH, IEEE 802.11b, IEEE 802.11g or another similar short range wireless communications protocol known in the art. In an example, the processing module 220 triggers the communication module 250 to establish a link based on detecting a shortage of remaining internal storage for physiological data storage associated with pathological episodes detected by the IMD 105. The processing module 220 can also trigger the communication module 250 when an episode with a high priority level is detected and data associated with the episode is captured. These examples of triggering communication with the external communication device 120 are based on management of physiological data retention. As will be discussed below, different retention or processing schemes can be employed to focus on retaining different types and amounts of data within the IMD 105.

At 620, the method 600 can optionally continue with the processing module 220 selecting certain portions of physiological data either just captured or previously stored in memory 240 to download to the external communication device 120 via the communication module 250. Implantable medical devices can prioritize data retention based on factors such as episode type. Table 3 depicts an example retention matrix based on episode priority.

TABLE 3

Episode Data Retention Matrix

| Episode Type | Priority | Minimum Number | Maximum Number |
|---|---|---|---|
| VF | 1 | 5 | 30 |
| Patient Triggered Monitor | 1 | 1 | 1 |
| VT/VT-1 | 2 | 3 | 25 |
| Cmd V | 3 | 0 | 2 |
| NonSust V | 3 | 1 | 2 |
| ATR | 4 | 1 | 3 |
| PMT | 4 | 1 | 3 |

In reference to the example retention matrix, depicted in Table 3, Cmd V stands for commanded therapy that includes therapy commanded via the programmer, such as commanded shock or commanded ATP schemes. NonSust V is a non-sustained episode that can include those tachy episodes in which therapy was inhibited for various reasons, such as a) the zone detection window did not remain satisfied for the programmed duration prior to therapy delivery or b) detection enhancement criteria indicated inhibition and the rate eventually dropped below the lowest tachy rate zone threshold. ATR refers to atrial episodes that include Atrial Tachy Response (ATR) events in which ATR fallback is triggered. PMT stands for pacemaker-mediated tachycardia (PMT) events, which are detected, for example, by counting 16 successive ventricular paces at the maximum Tracking Rate following atrial sensed events.

Programming the IMD 105 according to a retention matrix such as Table 3 enables the processing module 220 to prioritize how physiological data is handled once the internal memory is filled. For example, once the device memory 240 available for the episode data is filled, the IMD 105 can prioritize the types of stored episodes and overwrite or compress the stored episodes according to priority and minimum number of episodes stored.

The method 600 concludes at 630 with the communication module 250 transmitting physiological data to the external communication device 120. If the method 600 included operation 620, then only the data selected for transmission is transmitted to the external communication device 120 at 630. If no selection occurred, the processing module 220 can use a pre-defined process for selecting data to transmit out of the memory 240, such as priority, episode type, last-in-first-out, or first-in-first-out. If the communication link was initiated because of a particular episode, then the data collected associated with that episode can be transmitted first.

In certain examples, operation 630 can also include transmission of information regarding the compression technique used on the transmitted data. Transmitting information about the compression technique ensures that the external device is able to decode the compressed data properly.

Figure 7:
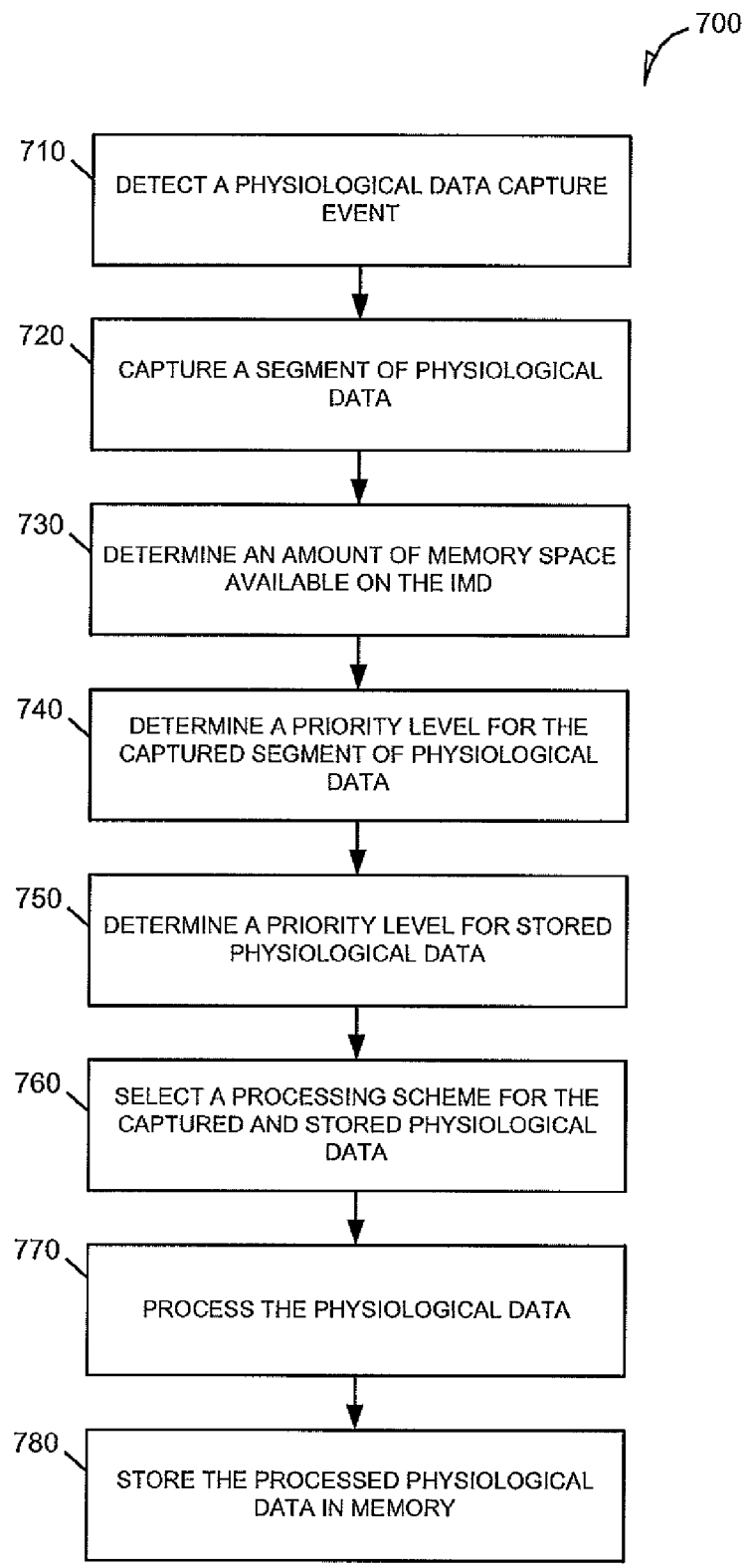
FIG. 7 is a flowchart illustrating an example method for managing physiological data collected by an IMD.

FIG. 7 is a flowchart illustrating an example method for managing physiological data collected by an IMD. A method 700 includes detecting a physiological data capture event 710, capturing a segment of physiological data 720, determining an amount of memory space available on an IMD 730, determining a priority level for the captured segment of physiological data 740, determining a priority level for stored physiological data 750, selecting a processing scheme for the captured and stored physiological data 760, processing the physiological data 770, and storing the processed physiological data in memory 780.

The method 700 begins at 710 with the IMD 105 detecting a physiological data capture event. In some examples, a capture event can occur upon detection of an episode that may or may not lead to a device response such as delivering a pacing pulse. In another example, the capture event can be triggered manually by the patient or based on a sensor 110 detecting some physiological parameter transgressing a set threshold. These additional capture events do not necessarily coincide with the delivery of therapy or even the identification of an episode. The IMD 105 can be configured to capture physiological data in response to detection of a data capture event. At 720, the method 700 continues with the physiological data monitor capturing data associated with the capture event detected at 710. Data capture can occur for a set period of time based on the capture event or for as long as the capture event remains active up to a maximum time period. In an example, the data capture results in a time-based, segment of the physiological data being captured and sent to the processing module 220 for further processing.

At 730, the method 700 continues with the processing module 220 determining the amount of memory space available on the IMD 105. Next, at 740, the processing module 220 determines a priority level for the captured segment of physiological data. In an example, determining priority can include classifying the episode or data capture event. In certain examples, determining priority can also include analyzing data from other physiological sensors 110 and determining the device response to the capture event, among other things. In a similar manner, the method 700 continues at 750 with the processing module 220 determining a priority level for any physiological data already stored in the memory 240. In some examples, determining the priority level of stored data can include simply referencing the priority level assigned to the stored data segment when it was previously stored in the memory 240. Priority levels for stored physiological data segments can be retained in a simple database, flat file or within the physiological data structure stored in memory 240.

Figure 8:
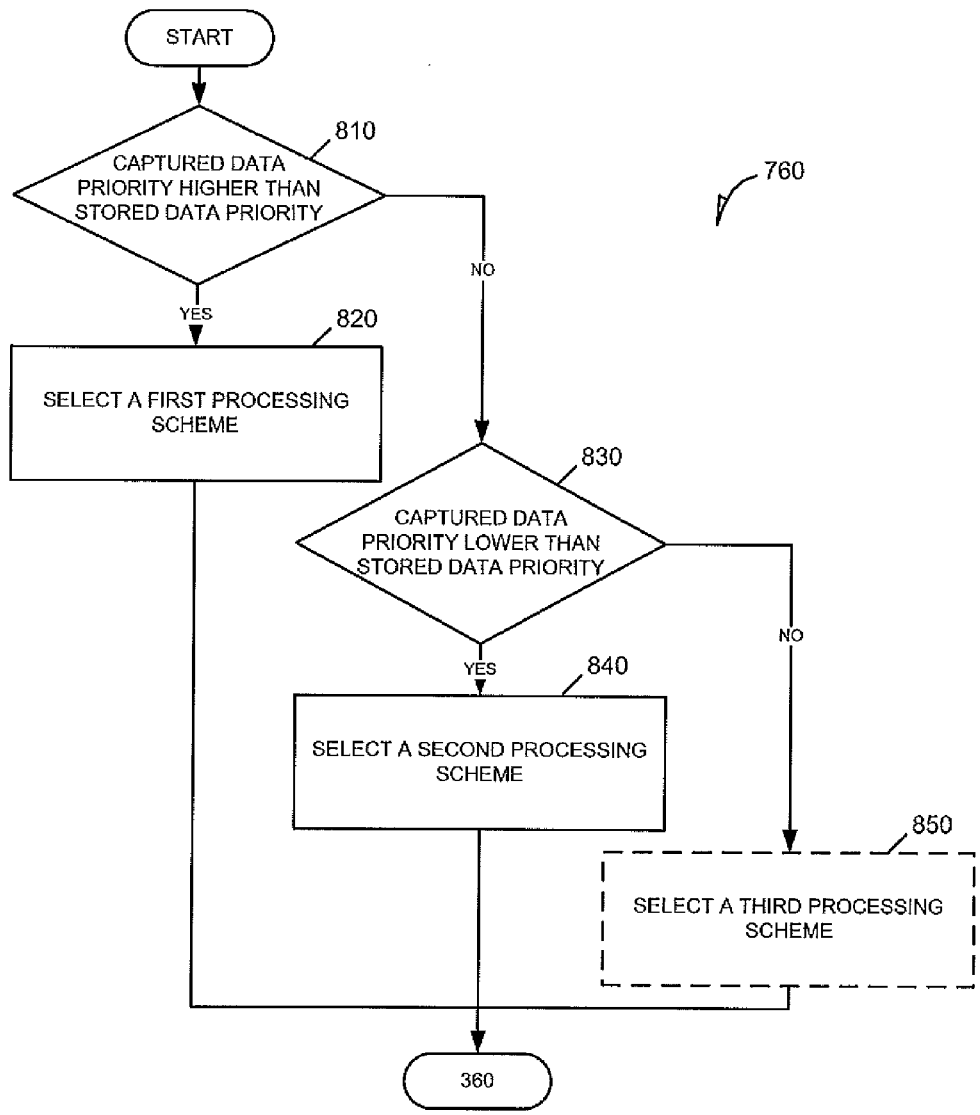
FIG. 8 is a flowchart illustrating an example method for selecting a processing scheme to process physiological data collected by an implantable medical device.

At 760, the method 700 continues with the processing module 220 selecting a processing scheme for the captured and stored physiological data. Selecting a processing scheme can include evaluation of the relative priorities and available storage space, among other things. In an example, a processing scheme can be as simple as storing the captured physiological data in memory with no compression and doing nothing to alter any stored physiological data segments. In another example, a process scheme can include applying a compression technique to the captured physiological data segment, applying a different compression technique to one or more stored physiological data segments, and attempting to transmit yet other physiological data segments to an external communication device 120 prior to storing the captured physiological data segment. FIG. 8, discussed in detail below, illustrates an example processing scheme selection process.

At 770, the method 700 concludes with the processing module 220 using the selected processing scheme to process the physiological data segments implicated by the processing scheme. As mentioned above, the processing scheme can direct the processing module 220 to store the processed data in the memory 240 or trigger the communication module 250 to establish a communication link to an external communication device 120 to download some or all of the physiological data segments.

FIG. 8 is a flowchart illustrating an example method for selecting a processing scheme to process physiological data collected by an IMD. A method 760 includes determining whether a captured physiological data segment or one or more stored physiological data segments have higher priority 810, 830 and then selecting a first 820, second 840, or third 850, processing scheme. The method 760 starts at 810 with the processing module 220 determining whether the newly captured physiological data segment is of higher priority than any of the physiological data segments stored in memory 240. If the newly captured physiological data segment is of higher priority, then a first processing scheme can be selected at 820. If the captured data is of lower priority than some of the physiological data segments stored in memory 240, then method 760 selects a second processing scheme at 840. If the priority of the captured data segment and the data segments stored in memory 240 are equal, then the method 760 can optionally select a third processing scheme at 850.

As discussed above, priorities can be assigned to each physiological data segment by analyzing any of the input parameters available to the IMD 105 at the time the data was captured. Additionally, a physiological data segment can also be prioritized based on previously captured physiological data segments. For example, if the newly captured data segment was captured under similar circumstances as the most recent previous data segment, then the newly captured data segment can be assigned a lower priority. As an example, if a first data segment was captured when a tachyarrhythmia was detected and a second data segment was also captured when a similar tachyarrhythmia was detected, the second data segment can be given a lower priority. A lower priority is particularly appropriate when multiple factors are similar, such as episode type, heart rate characterization, and device response.

In some examples, the IMD 105 can use the episode priority information to re-process physiological data segments previously stored in the memory 240. For example, if storage space within the memory 240 is critically low, the processor 225 can further compress the lowest priority physiological data segments to save additional storage space.

Figure 9:
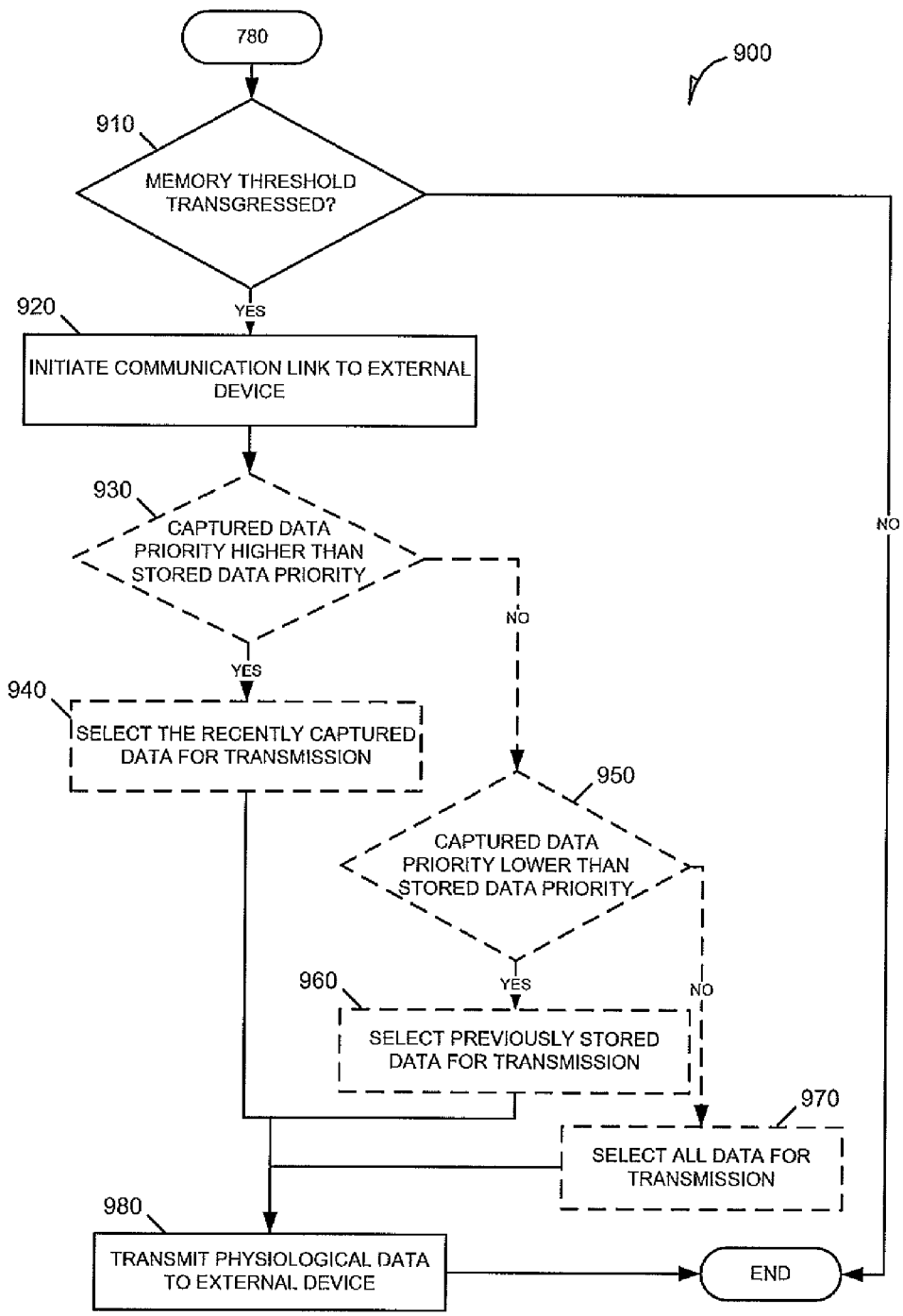
FIG. 9 is a flowchart illustrating an example method for initiating communication with an external device to download physiological data collected by an implantable medical device.

FIG. 9 is a flowchart illustrating an example method for initiating communication with an external device to download physiological data collected by an implantable medical device. A method 900 includes determining whether a memory threshold has been transgressed 910, initiating a communication link to an external device 920, and transmitting physiological data to the external device 980. Optionally, the method 900 can include determining whether the recently captured physiological data or stored physiological data has a higher priority 930, 950 and selecting physiological data for transmission 940, 960, 970. The method 900 illustrated in FIG. 9 indicates that this example starts after method 700 has finished storing recently captured physiological data. In another example, the method 900 can operate prior to storage of the currently captured physiological data. In this alternative scenario, the method 700 may not process operation 780, especially if the newly captured physiological data is transmitted to the external communication device 120. In yet another example, the method 900 can also operate in conjunction with or as a substitute to operations 730, 740, and 750.

In an example, the method 900 begins at 910 with the processing module 220 determining whether the amount of physiological data stored in the memory 240 has transgressed a pre-defined threshold. If the memory threshold has not been transgressed, indicating that the memory 240 has space for additional physiological data storage, then the method 900 finishes without any further processing. However, if the memory threshold is transgressed, then the method 900 continues at 920 with the communication module 250 initiating a communication link to the external communication device 120. Once the communication link with the external communication device 120 is established, the method 900 can continue at 980 with the communication module 250 transmitting physiological data collected by the IMD 105 to the external communication device 120. As discussed above, the communication link can operate over any short range wireless communication protocol, such as BLUETOOTH or IEEE 802.11n.

In certain examples, the communication module 250 will transmit data out of the memory 240 according to a first-in-first-out (FIFO) type of algorithm. Transmitting data out using a FIFO algorithm ensures that the oldest stored data is downloaded off the IMD 105 first. In another example, the communication module 250 can use a last-in-first-out (LIFO) algorithm for downloading data out of the memory 240. The LIFO algorithm ensures that the most recently stored data will be downloaded off the IMD 105 first. In yet another example, the communications module can use a priority-based algorithm for downloading data from the memory 240.

Using a priority-based algorithm ensures that the data considered by the treating physician or IMD 105 programmer to be the most important is downloaded off the IMD 105 first. One reason to be concerned about which portion of the collected physiological data to transmit first is that the IMD 105 is ambulatory and can move beyond the range of the wireless communication protocol at any time. The concern about wireless range is even applicable to devices connected via cellular (e.g., time division multiplexing, code division multiplexing, or GPRS) or some similar longer range communication protocols.

Optionally, the method 900 can include additional operations prior to transmitting the physiological data to the external communication device 120. In this example, the additional operations are used to select which physiological data segments will be transmitted to the external communication device 120 (or at least which physiological data segments to transmit first). After initiating a communication link at 920, the method 900 can continue at 930 with the processing module 220 determining whether the captured physiological data has a higher priority than any of the physiological data stored in the memory 240. If the captured physiological data has a higher priority, then the method 900 can continue at 940 with the processing module 220 selecting the newly captured physiological data for transmission to the external communication device 120.

If the newly captured data has a lower priority than some of the physiological data stored in memory 240, as determined at 950, then the method 900 can continue at 960 with the processing module 220 selecting at least a portion of the previously stored physiological data for transmission to the external communication device 120. At 950, if the processing module 220 determines that the newly captured physiological data and the stored physiological data all have the same priority level, then the method 900 continues at 970 with the processing module 220 selecting all the physiological data currently on the IMD 105 for transmission to the external communication device 120.

In some examples, the data structure used to store physiological data within the memory 240 can include a transmitted flag to indicate whether that particular episode data has been transmitted to an external device, such as the external communication device 120. The IMD 105 can use this flag as another method of managing the memory 240. For example, if new episode data is recorded and available space within memory 240 is running low, the processor 225 can delete episodes with the transmitted flag set to "transmitted," as this data is being retained off the IMD 105.

Figure 10:
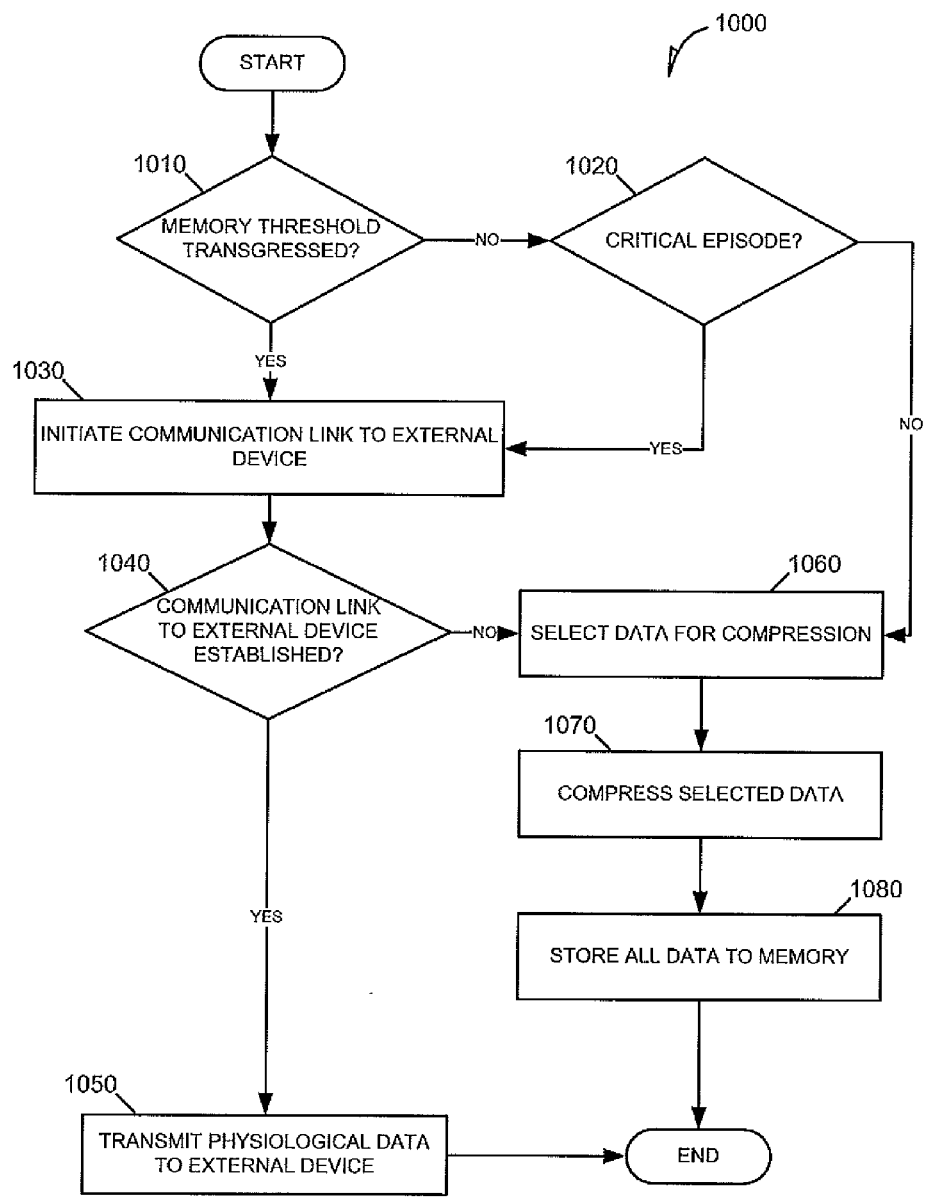
FIG. 10 is a flowchart illustrating an example method for managing physiological data collected by an implantable device through the use of various compression techniques and downloading data to an external device.

FIG. 10 is a flowchart illustrating an example method for managing physiological data collected by an implantable device through the use of various compression techniques and downloading data to an external device. A method 1000 includes determining whether a memory threshold is transgressed 1010, determining whether the captured physiological data is associated with a critical episode 1020, initiating a communication link to an external device 1030, determining whether a communication link is established to an external device 1040, transmitting physiological data to external device 1050, selecting data for compression 1060, compressing selected data 1070, and storing all data to memory 1080.

The method 1000 begins at 1010 with the processing module 220 determining whether the current amount of data stored in the memory 240 transgresses a memory threshold. The memory threshold transgression can be calculated using only the data already stored in the memory 240 or can include the newly captured physiological data. If the memory threshold has been transgressed, then the method 1000 continues at 1030 with the communication module 250 initiating a communication link to the external communication device 120. At 1020, the method 1000 includes another condition that can cause initiation of a communication link to the external communication device 120 at 1030. If the processing module 220 determines that the newly captured physiological data is associated with a critical episode, then the method 1000 will trigger the communication modtile 250 to initiate a communication link to the external communication device 120 at 1030. If the detected episode is critical, the communication link can be triggered regardless of whether the memory threshold has been transgressed. In certain examples, the IMD 105 can attempt to send all physiological data stored in the memory 240 while marking each episode remaining in the memory 240 appropriately as "transmitted" or "untransmitted." If additional storage space is require, the episode data marked as "transmitted" still stored within the memory 240 can be deleted or further compressed.

If the memory threshold has not been transgressed and the episode is not critical the method 1000 continues at 1060. At 1060, the processing module selects physiological data for compression. Physiological data is selected for compression to conserve space within the memory 240 as no communication link was established to download data off of the IMD 105. The selection process at 1060 includes any of the operations discussed above in relation to FIGS. 3-5 and 7-8. In certain examples, the physiological data selected for compression at 1060 can include new episode data, old episode data, or a combination of new and old episode data. At 1070, the method 1000 continues with the processing module 220 compressing the selected physiological data. Then at 1080, the method 1000 can conclude by storing all the physiological data processed at 1070 into the memory 240. In an example, the physiological data processed at 1070 and stored at 1080 can be the newly captured physiological data.

At 1040, the method 1000 continues with the communication module 250 determining if a communication link to the external communication device 120 has been established. If the communication link has been established, the method 1000 continues at 1050 with the communication module 250 transmitting physiological data from the IMD 105 to the external communication device 120 over a wireless communication protocol. Transmission of the physiological data can include any of the transmission algorithms described above in reference to FIGS. 6 and 9. If the communication module 250 is unable to establish a communication link with the external communication device 120, then the method 1000 continues at 1060, as described above. In certain examples, the selection of physiological data for compression, as well as the selected compression technique, can take into account the criticality of the episode and whether the current status of the memory 240 transgresses the memory threshold.

Compression Techniques

In the various examples described above the compression techniques have been discussed primarily in terms of relative compression levels or lossiness. This section includes a general description of data compression and some specific example techniques that can be used within the present subject matter.

Lossless versus lossy data compression is a way of describing the level of fidelity maintained by a particular compression technique. Lossless compression algorithms generally exploit statistical redundancy in a data pattern to represent the data pattern in less storage space than the original. Lossy data compression, also know as perceptual coding, can be used when some loss of fidelity is acceptable. A loss of fidelity can be accepted when the loss will not seriously impact the ability to perceive or interpret the resulting data. While lossless compression techniques are reversible (meaning the original data fidelity can be recovered), lossy compression techniques require accepting some loss of data in order to achieve higher compression ratios.

Lossy data compression can be as simple as sampling data over time or as complex as vector quantization, which involves modeling of probability density functions by the distribution of prototype vectors. In some examples, storing snippets of waveform data instead of storing the entire episode data is used as one of the available compression techniques for appropriate types of data. Table 2 provides a list of traditional lossless and lossy data compression techniques.

TABLE 2

Example Compression Techniques

| Lossless Data Compression | Lossy Data Compression |
|---|---|
| Run-length Encoding | Discrete Cosine Transformation |
| Dictionary Coders | Fractal Compression |
| Burrows-Wheeler Transform | Wavelet Compression |
| Prediction by Partial Matching | Vector Quantization |
| Context Mixing | Linear Predictive Coding |
| Dynamic Markov Compression | Modulo-N Code for Correlated Data |
| Entropy Encoding | A-law Compander |

Example External Device and Machine-Readable Medium

Figure 11:
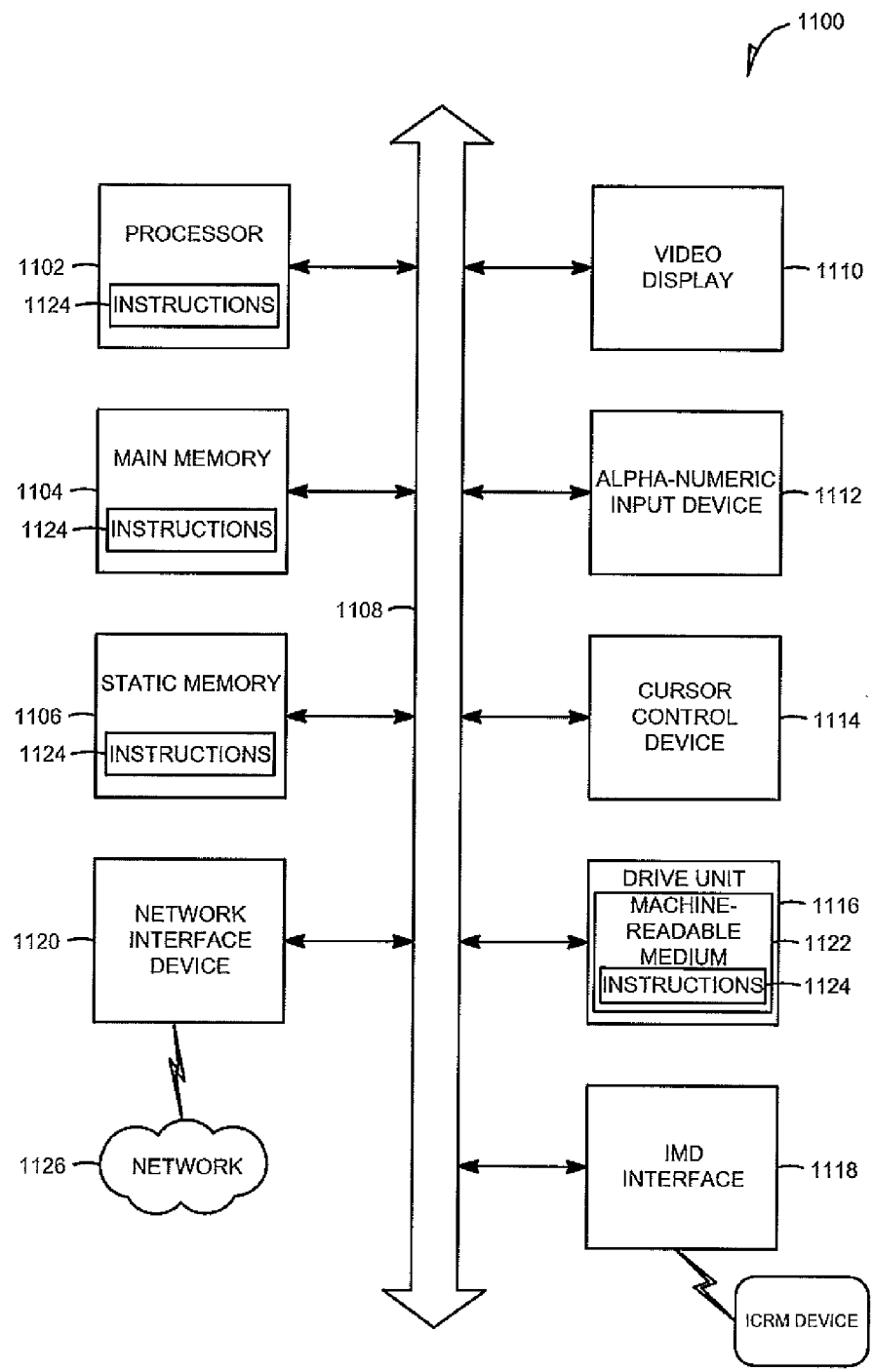
FIG. 11 is a block diagram illustrating an example of an external programming and diagnostic computer.

FIG. 11 is a block diagram illustrating an example of an external communication and storage device. The system 1100 is a machine in the example form of a computer system 1100 within which instructions, for causing the machine to assist in the performance of any one or more of the methodologies discussed herein, may be executed. In certain examples, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the machine can include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 can further include a video display unit 1110 (e.g., a liquid crystal display (LCD) or a cathode ray tube (CRT)). The computer system 1100 also includes an alphanumeric input device 1112 (e.g., a keyboard), a user interface (UI) navigation device 1114 (e.g., a mouse), a disk drive unit 1116, an implantable medical device interface 1118, and a network interface device 1120. The implantable medical device interface can include a wired or wireless data connection with an implantable medical device. In certain examples, the system 1100 includes both a wired and a wireless data connection with an implantable medical device. In an example, the implantable medical device (IMD) interface allows information stored in the IMD to be downloaded to the computer system 1100 for storage and/or retransmission to a treating physician or patient management system. In an example, the information downloaded from the IMD can be displayed on the video display unit 1110. In another example, the information downloaded can be processed by the processor 1102 prior to display on the video display unit 1110. In an example, the IMP interface can also upload information, including programming parameters for an implantable CRM device, back into the IMD.

Machine-Readable Medium

The disk drive unit 1116 includes a machine-readable medium 1122 on which can be stored one or more sets of instructions and data structures (e.g., software) 1124 embodying or utilized by any one or more of the methodologies or functions described herein. The instructions 1124 can also reside, completely or at least partially, within the main memory 1104 or within the processor 1102 during execution thereof by the computer system 1100, the main memory 1104 and the processor 1102 also constituting machine-readable media.

While the machine-readable medium 1122 can be shown in an example embodiment to be a single medium, the term "machine-readable medium" can include a single medium or multiple media (e.g., a centralized or distributed database, or associated caches and servers) that store the one or more instructions or data structures. The term "machine-readable medium" can include any tangible medium that is capable of storing, encoding or carrying instructions for execution by the machine and that cause the machine to perform any one or more of the methodologies of the present application, or that is capable of storing, encoding or carrying data structures utilized by or associated with such instructions. The term "machine-readable medium" can include, but need not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks including internal hard disks and removable disks; magneto-optical disks; and CD-ROM and DVD-ROM disks.

Transmission Medium

The instructions 1124 can further be transmitted or received over a communications network 1126 using a transmission medium. The instructions 1124 can be transmitted using the network interface device 1120 and any one of a number of transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi and WiMax networks).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A system for adaptively managing physiological data within a medical device, the system comprising:
   a medical device, the device comprising:
   a physiological data monitor to monitor a physiological data parameter;
   a memory circuit to store data collected by the physiological data monitor;
   a processor circuit, coupled to the physiological data monitor and the memory circuit, the processor configured to, detect a pathological episode using the monitored physiological data parameter;

classify the pathological episode as one of a plurality of specified episode types;

capture, from the physiological data monitor, a segment of physiological data associated with the pathological episode;

select, in response to the classification of the pathological episode and using the classified episode type, a compression technique from a plurality of compression techniques to process the captured segment of physiological data;

process the captured physiological data using the selected compression technique to produce a processed segment of physiological data; and store the processed segment of physiological data in the memory circuit for later use.

2. The system of claim 1, wherein the processor is configured to:

determine an amount of remaining storage space available within the memory circuit; and select a compression technique, from a plurality of compression techniques using the amount of remaining storage space available within the memory circuit.

3. The system of claim 1, wherein the processor is configured to:

determine a device response to the pathological episode; and select a compression technique from a plurality of compression techniques using the determined device response to the pathological episode.

4. The system of claim 3, wherein the processor is configured to select the compression technique from a plurality of compression techniques using a result of evaluating a specified relationship between the device response and the episode type.

5. The system of claim 4, wherein the processor is configured to receive the specified relationship between the device response and the episode type from an external source.

6. The system of claim 1, wherein the processor is configured to:

characterize a detected heart rate using a comparison of atrial versus ventricular rates to produce an AV comparison; and select the compression technique from the plurality of compression techniques using the AV comparison.

7. The system of claim 6, wherein the processor is configured to:

determine a device response to the pathological episode; and select a compression technique from a plurality of compression techniques using the determined device response to the pathological episode and the AV comparison.

8. The system of claim 1, including an external data storage and communication device to receive physiological data stored in the memory circuit; and wherein the processor is configured to:

initiate, based on detecting a low memory circuit space condition, a communication link to the external data storage and communication device; and transmit a portion of the physiological data stored in the memory circuit.

9. The system of claim 8, wherein the processor is configured to transmit a portion of the physiological data stored in the memory circuit by transmitting the oldest data to the external data storage and communication device first.

10. The system of claim 1, wherein the processor is configured to determine a priority level for the segment of physiological data using the determined episode type.

11. The system of claim 10, wherein the processor is configured to select the compression technique using the determined priority level for the segment of physiological data.

12. A method for adaptively managing physiological data within a medical device, the method comprising:

monitoring a physiological data parameter;

detecting a pathological episode using the monitored physiological data parameter;

classifying the pathological episode as one of a plurality of specified episode types;

capturing a segment of physiological data associated with the pathological episode;

selecting, in response to the classification of the pathological episode and using the classified episode type, a compression technique from a plurality of compression techniques to process the captured segment of physiological data;

processing the captured physiological data using the selected compression technique to produce a processed segment of physiological data; and storing the processed segment of physiological data for later use.

13. The method of claim 12, wherein the selecting the compression technique further includes determining an amount of remaining storage space available within the medical device and using the amount of remaining storage space to select the compression technique.

14. The method of claim 12, further comprising determining a device response to the pathological episode; and wherein the selecting the compression technique uses the device response to the pathological episode.

15. The method of claim 14, wherein the selecting the compression technique includes:

selecting a first compression technique when the device response includes delivering shock;

selecting a second compression technique when the device response includes anti-tachycardia pacing;

selecting a third compression technique when the device response includes diverting a therapy; and wherein the first compression technique provides less compression than the second compression technique and the second compression technique provides less compression than the third compression technique.

16. The method of claim 14, wherein the selecting the compression technique includes using a result of evaluating a specified relationship between the device response and the episode type.

17. The method of claim 16, wherein the selecting the compression technique includes receiving the specified relationship between the device response and the episode type from an external source.

18. The method of claim 12, wherein the selecting the compression technique includes characterizing a detected heart rate using a comparison of atrial versus ventricular rate to produce an AV comparison; and using the AV comparison to select the compression technique from the plurality of compression techniques.

19. The method of claim 18, wherein the selecting the compression technique includes determining a device response to the pathological episode; and wherein the selecting the compression technique includes using the device response to the pathological episode and the AV comparison.

20. The method of claim 12, wherein the storing the processed segment of physiological data includes:
- initiating, based on detecting a low memory circuit space condition, a communication link to an external data storage and communication device; and
- transmitting a portion of the physiological data stored in the memory circuit.

21. The method of claim 20, wherein the transmitting the portion of the physiological data stored in the memory circuit transmits the oldest data to the external data storage and communication device first.

\* \* \* \* \*